(12) United States Patent
Anand

(10) Patent No.: US 9,924,983 B2
(45) Date of Patent: Mar. 27, 2018

(54) SPINAL CORRECTION METHOD AND SYSTEM

(71) Applicant: Warsaw Orthopedic, Inc., Warsaw, IN (US)

(72) Inventor: Neel Anand, Los Angeles, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/619,965

(22) Filed: Feb. 11, 2015

(65) Prior Publication Data
US 2016/0228160 A1    Aug. 11, 2016

(51) Int. Cl.
*A61B 17/88* (2006.01)
*A61B 17/70* (2006.01)
*A61B 17/68* (2006.01)

(52) U.S. Cl.
CPC ...... *A61B 17/7086* (2013.01); *A61B 17/7083* (2013.01); *A61B 2017/681* (2013.01)

(58) Field of Classification Search
CPC .......... A61B 17/8605–17/866; A61B 17/7001; A61B 17/7032–17/7046; A61B 17/7086; A61B 17/7083; A61B 17/681; A61B 17/7011; A61B 17/7013
See application file for complete search history.

(56) References Cited

U.S. PATENT DOCUMENTS

| 2005/0277934 A1* | 12/2005 | Vardiman | A61B 17/7083 606/914 |
| 2008/0177317 A1* | 7/2008 | Jackson | A61B 17/7026 606/254 |
| 2008/0269805 A1* | 10/2008 | Dekutoski | A61B 17/7004 606/279 |
| 2009/0198281 A1* | 8/2009 | Rice | A61B 17/7031 606/279 |
| 2011/0196426 A1* | 8/2011 | Peukert | A61B 17/7083 606/279 |
| 2015/0112392 A1* | 4/2015 | Anand | A61B 17/7011 606/279 |

* cited by examiner

Primary Examiner — Jacqueline Johanas
Assistant Examiner — Tessa Matthews

(57) ABSTRACT

A method for treating a spine, comprises the steps of fastening a first fastener to a first portion of vertebrae, a second fastener to a second portion of vertebra, and a third fastener to a third portion of vertebrae, wherein the second portion of vertebra is between the first and third vertebra; providing a longitudinal element having a first portion and a second portion; passing the first portion of the longitudinal element through the second and third fasteners such that the second portion of the longitudinal element extends from the second fastener through the third fastener; bending the first portion of the longitudinal element to a selected curvature; and moving the second portion of the longitudinal element through the second fastener to the first fastener after the first portion of the longitudinal element has been passed through the second and third fasteners. Systems and instruments are disclosed.

17 Claims, 11 Drawing Sheets

SPINAL CORRECTION METHOD AND SYSTEM

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ implants that are manipulated for engagement with vertebrae to position and align one or more vertebrae. This disclosure describes an improvement over these prior art technologies.

SUMMARY

In one embodiment, a method for treating a spine is provided. The method comprises the steps of: fastening at least one fastener with a first portion of vertebrae and at least one fastener with a second portion of the vertebrae; providing a longitudinal element having a first portion and a second portion; moving the longitudinal element along the at least one fastener of the first portion of the vertebrae such that the longitudinal element extends from adjacent the at least one fastener of the first portion of the vertebrae; bending the first portion of the longitudinal element to a selected curvature; and moving the longitudinal element along the portions of the vertebrae such that the second portion of the longitudinal element is disposed with the at least one fastener of the second portion of the vertebrae and the first portion of the longitudinal element is disposed with the at least one fastener of the first portion of the vertebrae. In some embodiments, systems and instruments are disclosed.

BRIEF DESCRIPTION OF THE DRAWINGS

The present disclosure will become more readily apparent from the specific description accompanied by the following drawings, in which.

DETAILED DESCRIPTION

Figure 1:
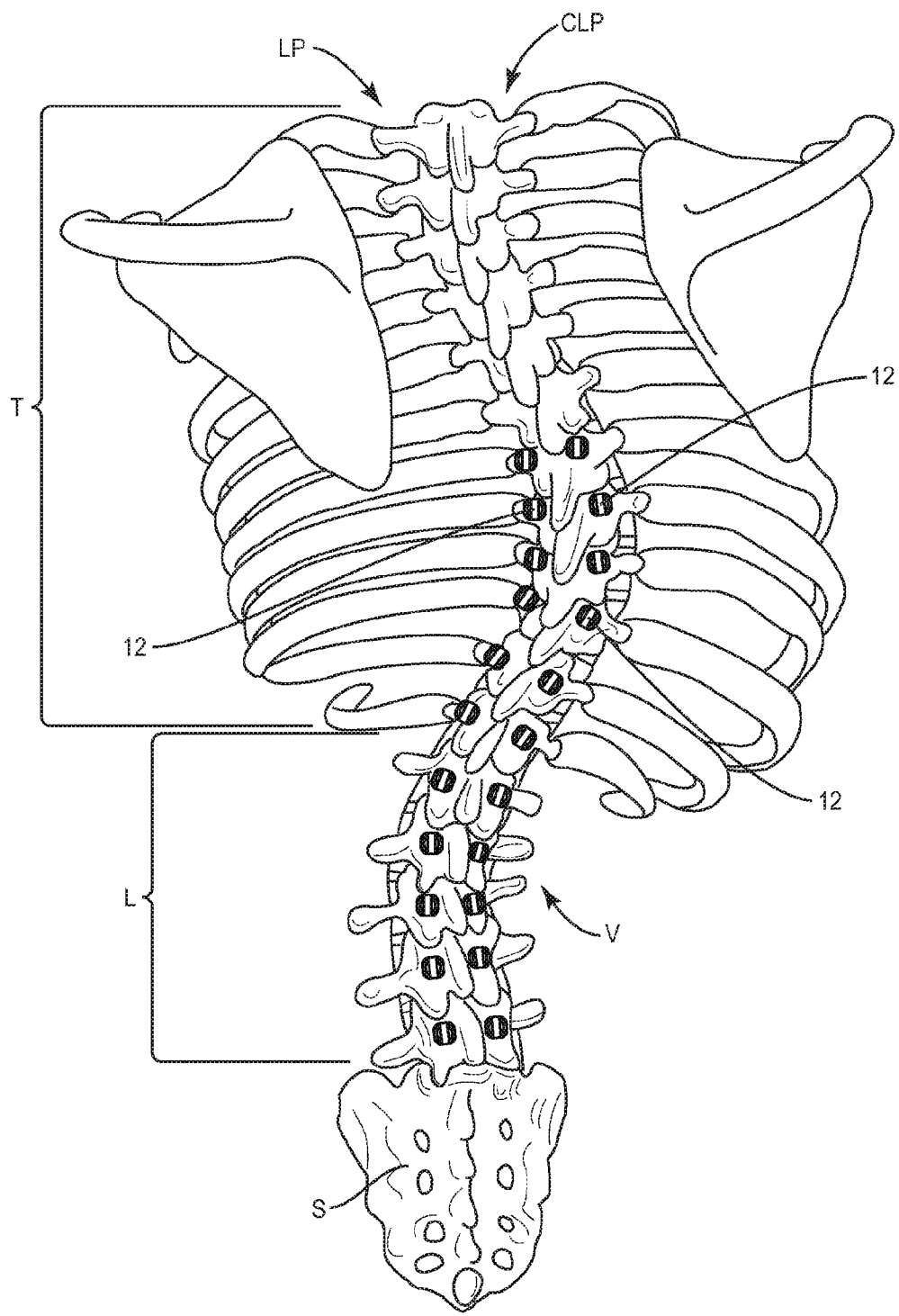
FIG. 1 is a plan view of components of one embodiment of a system in accordance with the principles of the present disclosure disposed with vertebrae.

The exemplary embodiments of the spinal correction system and related methods of use disclosed are discussed in terms of medical devices for the treatment of musculoskeletal disorders and more particularly, in terms of a spinal correction system and method that facilitates connection of at least one implant with vertebrae to position and align one or more vertebrae for treatment of a spine. In some embodiments, the spinal correction system can include instruments such as implant supports, inserters, and rod grippers, which can be used to introduce a longitudinal element such as a rod to a bone fastener, such as a bone anchor or bone screw. For example, an instrument can include an extender having bone anchor attachment features on one or both sides of the instrument. In some embodiments, the extender may be used with or include an inserter to introduce a spinal rod into a bone fastener.

In one embodiment, a method for spinal correction includes maintaining the spinal curvature after a spinal rod is passed percutaneously along the spine. In one embodiment, a method for spinal correction is provided that facilitates passing a spinal rod along the spine between the lumbar and thoracic spine the entire length of the thoracolumbar construct from a top to a bottom. In one embodiment, a method for spinal correction is provided that facilitates maintaining an appropriate shape of the spinal rod when the spinal rod is seated into a plurality of bone screws thereby avoiding flatback syndrome. In one embodiment, a method for spinal correction avoids passing the spinal rod above the fascia thereby avoiding having to cut and/or dissect the fascia round the spinal rod.

In one embodiment, a method for spinal correction includes bending a full thoracolumbar spinal rod with a gentle bend on each end of a spinal rod. In one embodiment, the method for spinal correction includes starting in the middle of the construct, such as, for example, T12 and passing a spinal rod from an extender to a most caudad extender and continue to push the spinal rod and grab the spinal rod with a rod gripper and pull the spinal rod out of the extender. In one embodiment, the method for spinal correction includes, bending the spinal rod extending from the extender to a desired lumbar curvature and unhooking the inserter from the spinal rod at T12 and re-attaching to the spinal rod at the portion extending from the caudad extender. In one embodiment, the method for spinal correction disposes the cephalad portion of the spinal rod at T12 below the fascia, and allows the spinal rod to pass through 111 and further cephalad ensuring that the rod remains below the fascia. In one embodiment, the method for spinal correction provides a spinal rod construct having a substantial match to the desired angle to a thoracic curvature of the patient.

In one embodiment, a method for spinal correction is provided that facilitates bending a spinal rod prior to implantation thereby allowing the bent spinal rod to be passed along the entire construct. In one embodiment, the method for spinal correction provides for bending the spinal rod in situ after implantation. In one embodiment, the method for spinal correction includes starting with a straight spinal rod in the lower thoracic region, passing the spinal rod through the lumbar extenders and bending the spinal rod into the proper angle with the upper portion of the rod remaining in the extenders in the lower portion of the construct. In one embodiment, the method for spinal correction provides passing the spinal rod back up through the thoracic extenders to the top of the construct.

In one embodiment, a method for spinal correction is provided with a system for posterior screw and rod placement and manipulation for deformity correction. The method includes use of multi-axial or poly-axial pedicle screws placed minimally invasively with a removable extension that guides placement of a longitudinal rod with a selected sagittal curve to control spine curvature in lower thoracic and lumbar regions. In some embodiments, interbody implants, bone screws and spinal rods are provided as a stable construct for deformity correction and fusion.

In one embodiment, the system is employed with a method for deformity correction, such as, for example, correction of scoliosis or kyphosis using a construct of implants including fasteners, such as, for example, multi-axial pedicle screws, and manipulating the implants using implant supports, such as, for example, extenders. In one embodiment, the system is employed with a method for spinal treatment, such as, for example, correction of a lumbar scoliosis. In some embodiments, the system is employed with a method to efficiently correct various deformity pathologies in sagittal, coronal and axial planes of vertebrae by using screws and reduction instruments.

In some embodiments, the method is used with surgical navigation, such as, for example, fluoroscope or image guidance. In one embodiment, one or all of the components of the surgical system are disposable, peel-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-11, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites, depending on the particular application and/or preference of a medical practitioner. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TOP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with a minimally invasive procedure, including percutaneous techniques, and mini-open surgical techniques to deliver and introduce instrumentation and/or an implant, such as, for example, a bone fastener, for a correction treatment at a surgical site within a body of a patient, for example, a section of a spine to treat various spine pathologies, such as, for example, kyphosis. In some embodiments, spinal correction system 10 may comprise various instruments, such as, for example, inserters, extenders, reducers, spreaders, distractors, blades, clamps, forceps, elevators and drills, which may be alternately sized and dimensioned, and arranged as a kit.

Figure 2:
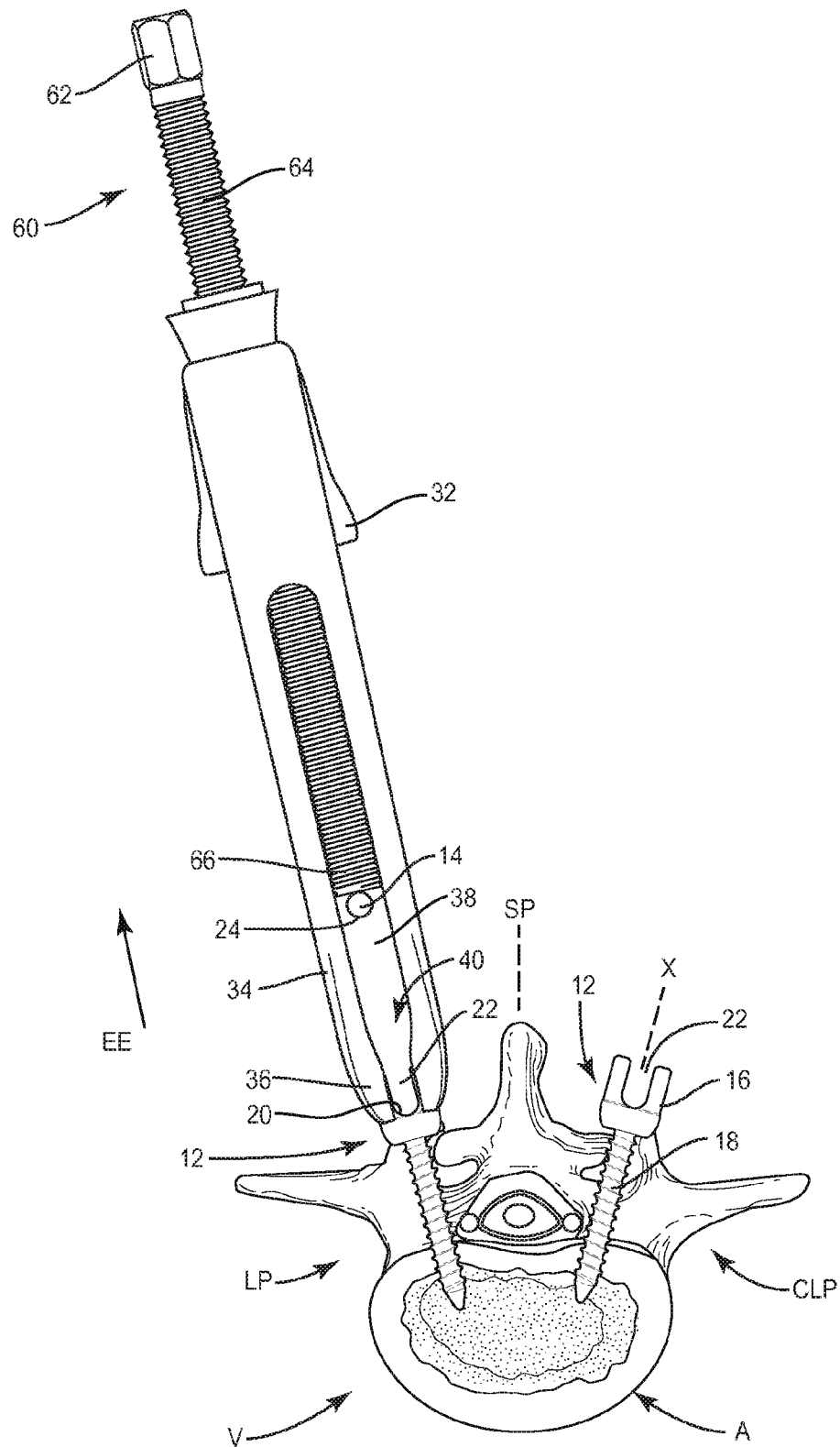
FIG. 2 is an axial view of components of one embodiment of a system in accordance with the principles of the present disclosure disposed with vertebrae.
Figure 3:
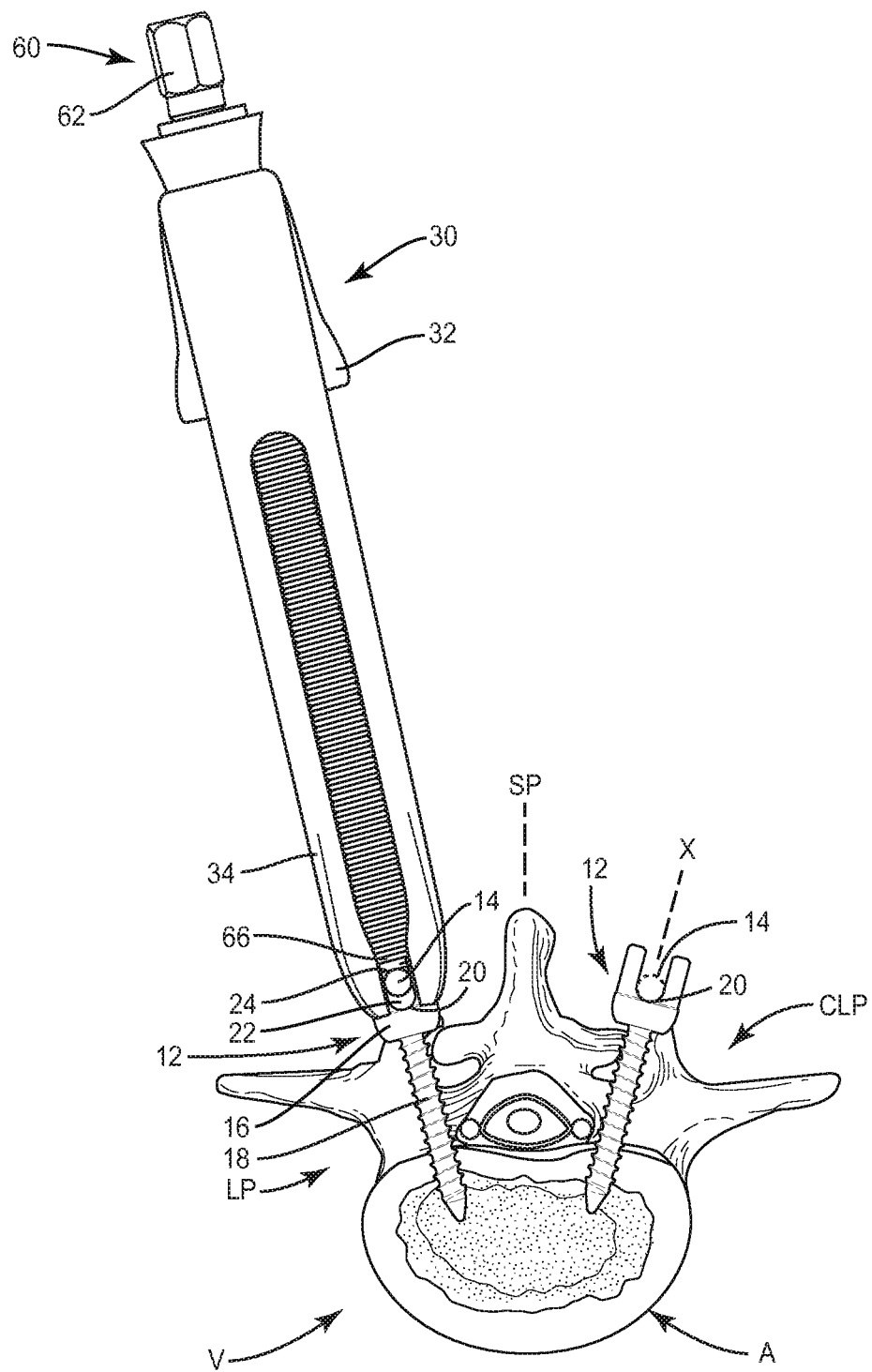
FIG. 3 is an axial view of the components shown in FIG. 2.
Figure 4:
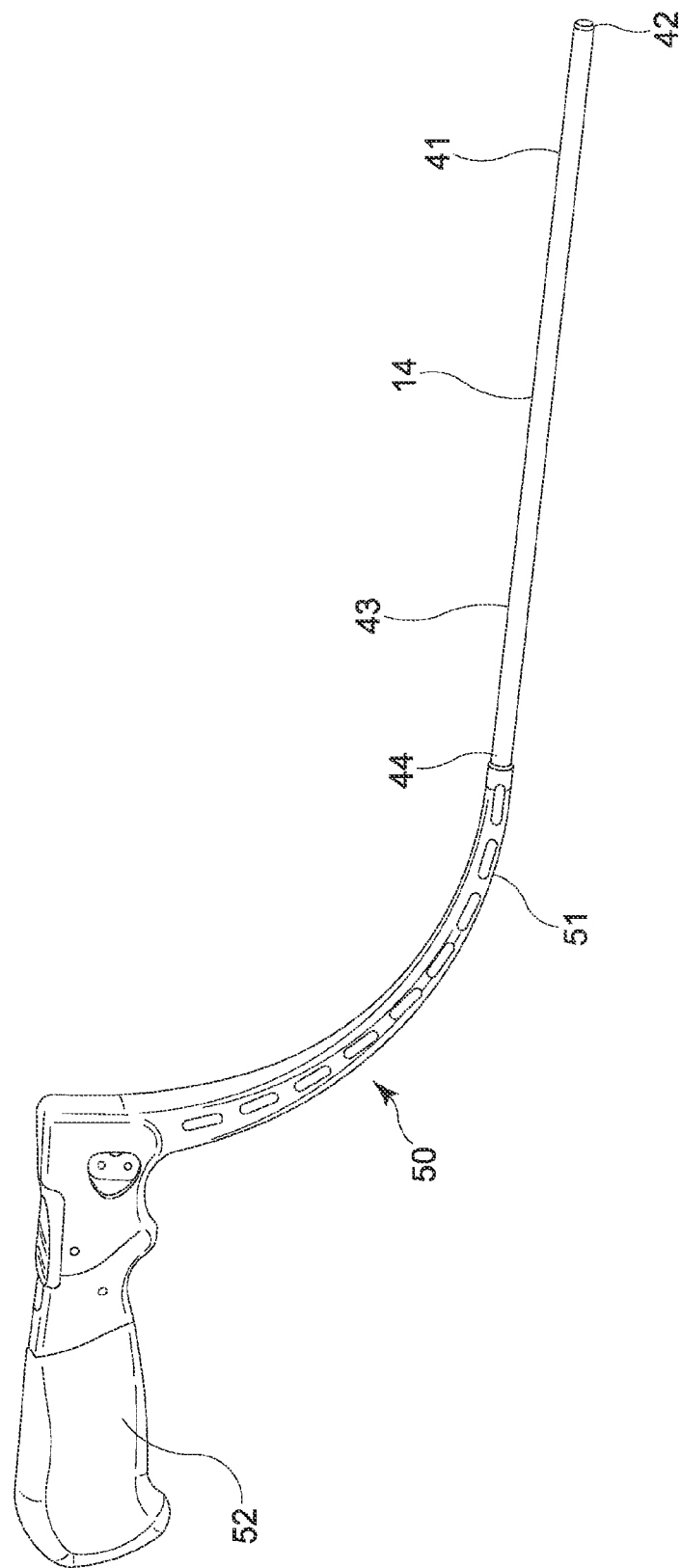
FIG. 4 is a perspective view of components of one embodiment of a system in accordance with the principles of the present disclosure.

Spinal correction system 10 includes a fastener, such as, for example, a poly-axial or multi-axial bone screw (MAS) 12, as shown in FIGS. 1-3, that connects a longitudinal element, such as, for example, a spinal rod 14, as shown in FIG. 4, to tissue, such as, for example, vertebrae V and/or components of spinal correction system 10, such as, for example, connectors, plates and other constructs, as will be described. In one embodiment, at least one fastener is fastened with a first portion of vertebrae V and at least one fastener is fastened with a second portion of the spine. In one embodiment, a plurality of fasteners is fastened with a first portion of vertebrae V, which includes lumbar vertebrae, such as, for example, vertebral levels L1-L5. In one embodiment, a plurality of fasteners is fastened with a first portion of vertebrae V, which includes thoracic vertebrae, such as, for example, vertebral levels T7-T12. Each MAS 12 defines a longitudinal axis X, as shown in FIGS. 2 and 3. MAS 12 comprises a first element, such as, for example, a receiver 16 and a second element, such as, for example, an elongated shaft 18 configured for penetrating tissue.

Shaft 18 has a cylindrical cross section configuration and includes an outer surface having an external thread form. In some embodiments, the external thread form may include a single thread turn or a plurality of discrete threads. In some embodiments, other engaging structures may be located on shaft 18, such as, for example, a nail configuration, barbs, expanding elements, raised elements and/or spikes to facilitate engagement of shaft 18 with tissue, such as, for example, vertebrae V.

In some embodiments, all or only a portion of shaft 18 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 18 may include one or a plurality of openings. In some embodiments, all or only a portion of the outer surface of shaft 18 may have alternate surface configurations to enhance fixation with tissue such as, for example, rough, arcuate, undulating, mesh, porous, semi-porous, dimpled and/or textured. In some embodiments, all or only a portion of shaft 18 may be disposed at alternate orientations, relative to the longitudinal axis, such as, for example, transverse, perpendicular and/or other angular orientations such as acute or obtuse, co-axial and/or may be offset or staggered. In some embodiments, all or only a portion of shaft 18 may be cannulated.

Receiver 16 includes a pair of spaced apart arms having an inner surface 20 that defines an implant cavity, such as, for example, a U-shaped passageway 22. Passageway 22 is configured for disposal of an implant, such as, for example, spinal rod 14. In some embodiments, all or only a portion of passageway 22 may have alternate cross section configurations, such as, for example, oval, oblong, triangular, square, polygonal, irregular, uniform, non-uniform, offset, staggered, and/or tapered. In some embodiments, the arms of receiver 16 may be disposed at alternate orientations, relative to axis X, such as, for example, transverse, perpendicular and/or other angular orientations such as acute or obtuse, co-axial and/or may be offset or staggered.

MAS 12 has a multi axial configuration such that receiver 16 is rotatable to a selected angle through and within an angular range relative to axis X in a plurality of planes that lie in a cone configuration. The area and/or volume defined by the cone configuration is defined by the range of motion of receiver 16 about axis X. In one embodiment, a receiver 16 is movable relative to a shaft 18 of at least one MAS 12. In one embodiment, receiver 16 is rotated and/or pivoted relative to a shaft 18 of at least one MAS 12 such that inner surface 20 rotates about and relative to an outer surface 24 of spinal rod 14 to provide coronal plane correction and/or provide tension on vertebrae V. Inner surface 20 includes a thread form configured for engagement with a coupling member (not shown), such as, for example, a set screw. The set screw is threaded with receiver 16 to attach, provisionally fix and/or lock spinal rod 14 with MAS 12, as described.

In some embodiments, spinal correction system 10 includes one or more of fasteners that may be engaged with tissue in various orientations, such as, for example, series, parallel, offset, staggered and/or alternate vertebral levels. In some embodiments, the fasteners may comprise sagittal angulation screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Spinal rod 14 has a cylindrical cross section configuration. In some embodiments, spinal correction system 10 may include one or a plurality of spinal rods, which may be relatively disposed in a side by side, irregular, uniform, non-uniform, offset and/or staggered orientation or arrangement. In some embodiments, spinal rod 14 can have a uniform thickness/diameter. In some embodiments, spinal rod 14 may have various surface configurations, such as, for example, rough, threaded for connection with surgical instruments, arcuate, undulating, dimpled, polished and/or textured. In some embodiments, the thickness defined by spinal rod 14 may be uniformly increasing or decreasing, or have alternate diameter dimensions along its length. In some embodiments, spinal rod 14 may have various cross section configurations, such as, for example, oval, oblong, triangular, rectangular, square, polygonal, irregular, uniform, non-uniform, variable and/or tapered. In some embodiments, spinal rod 14 may have various lengths. In some embodiments, the longitudinal element may include one or a plurality of tethers.

In one embodiment, spinal rod 14 comprises first portion 41 having an end 42 and second portion 43 having an end 44. In one embodiment, portions 41, 43 comprise varying lengths of spinal rod 14. In such embodiments, for example, portion 41 is longer than portion 43 or vice versa. In one embodiment, portions 41, 43 each comprise longitudinal halves of spinal rod 14. In one embodiment, end 42 is a caudally leading end during insertion, and end 44 is a cephalically leading end during insertion. In one embodiment, end 42 is a cephalically leading end during insertion, and end 44 is a caudally leading end during insertion.

In some embodiments, the longitudinal element may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of the longitudinal element includes movement in a lateral or side to side direction and prevents expanding and/or extension in an axial direction. In some embodiments, all or only a portion of the longitudinal element may have a semi-rigid, rigid or elastic configuration, and/or have elastic properties, such as the elastic properties corresponding to the material examples described above. In some embodiments, the longitudinal element may be compressible in an axial direction.

Figure 6:
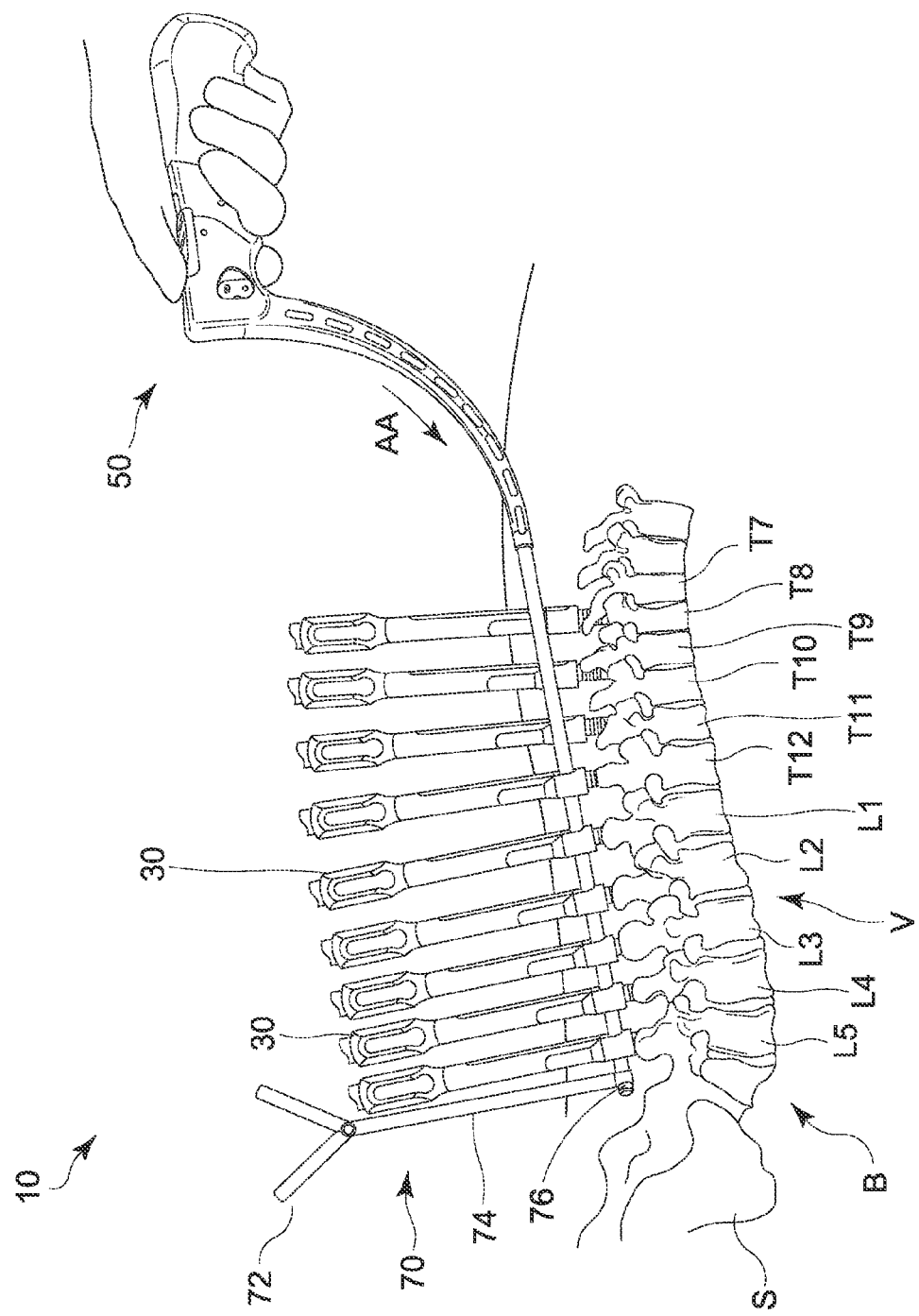
FIG. 6 is a plan view of components of one embodiment of a system in accordance with the principles of the present disclosure disposed with vertebrae.
Figure 7:
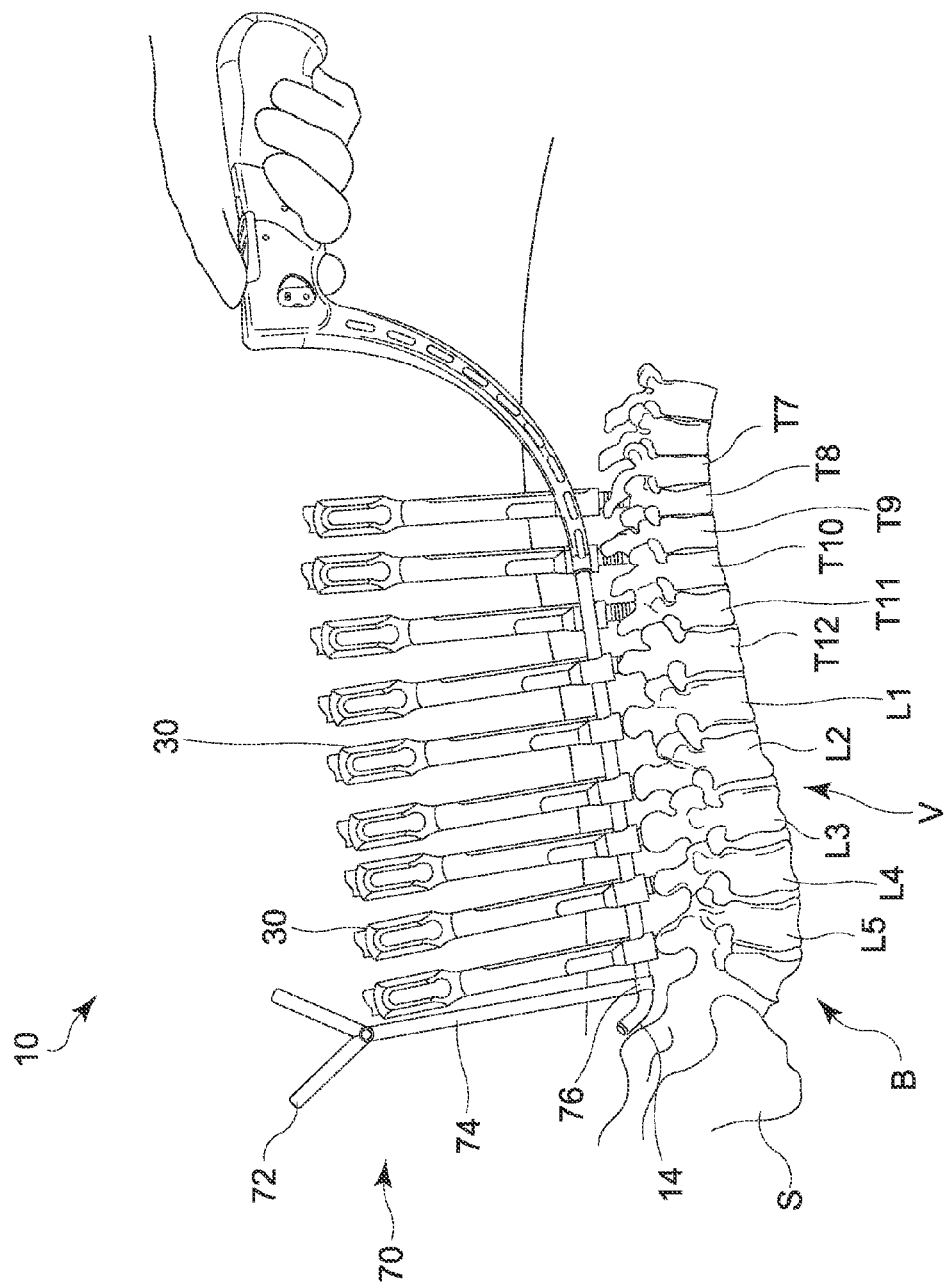
FIG. 7 is a plan view of the components shown in FIG. 6.
Figure 8:
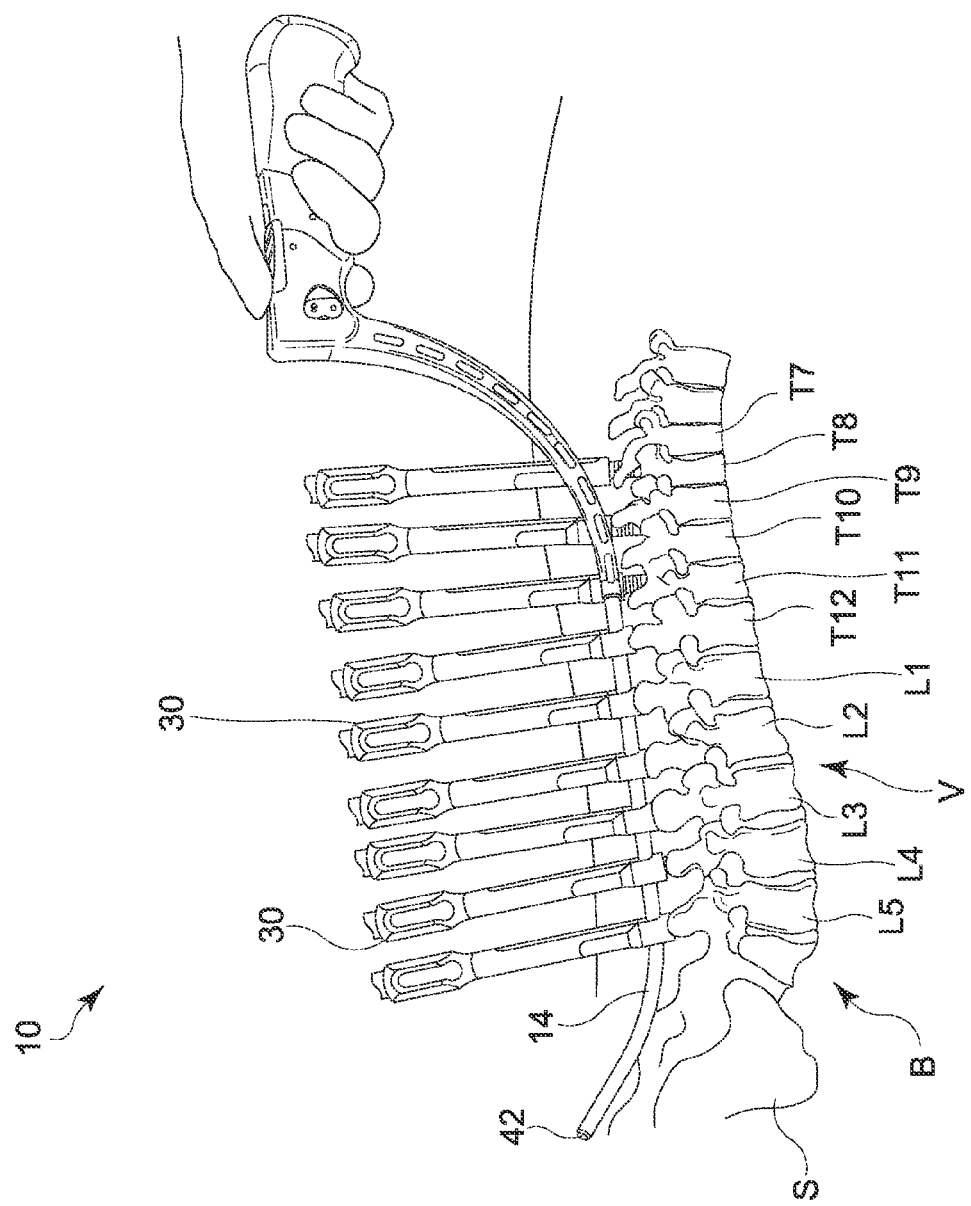
FIG. 8 is a plan view of components of one embodiment of a system in accordance with the principles of the present disclosure disposed with vertebrae.
Figure 9:
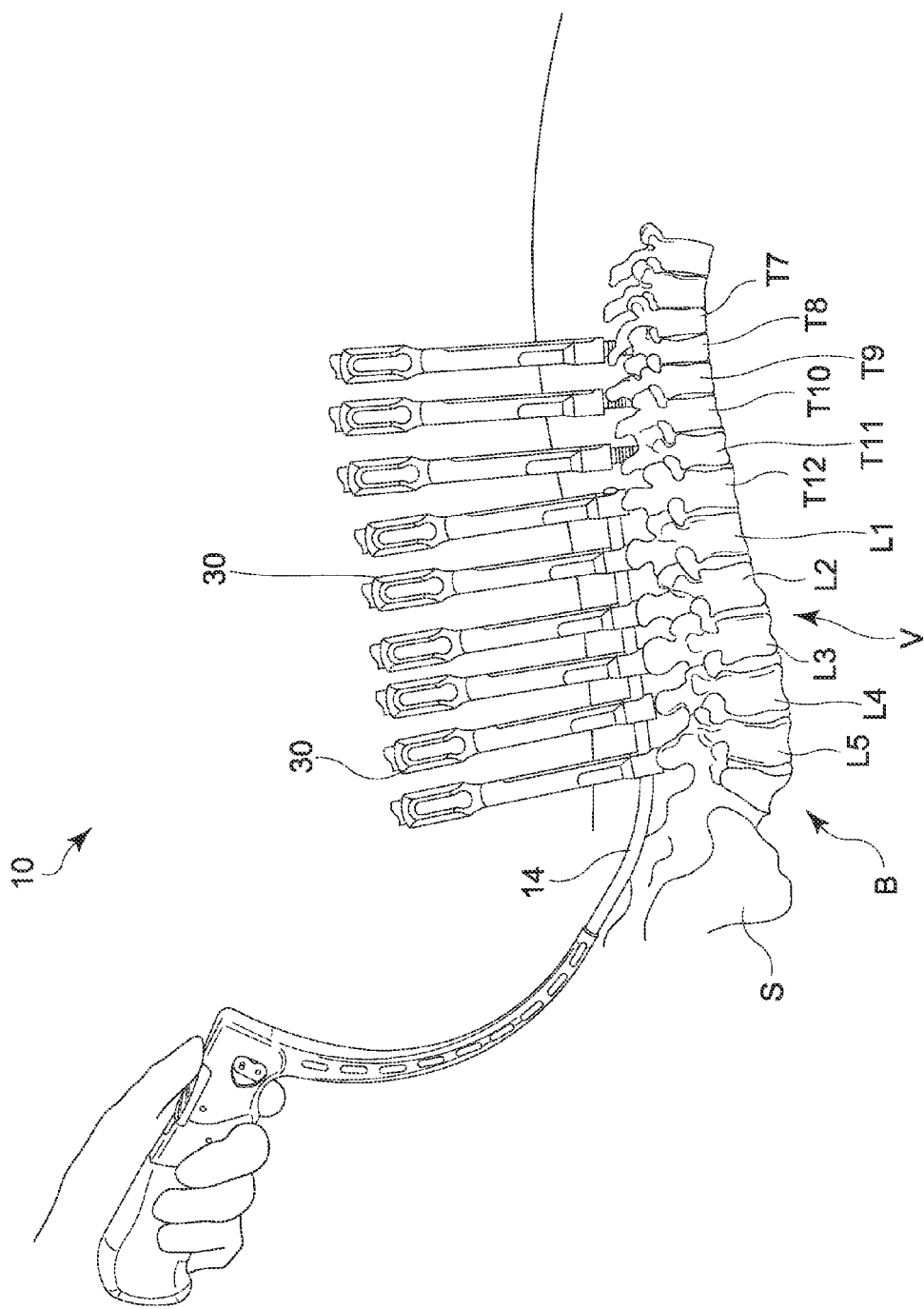
FIG. 9 is a plan view of components of one embodiment of a system in accordance with the principles of the present disclosure disposed with vertebrae.
Figure 10:
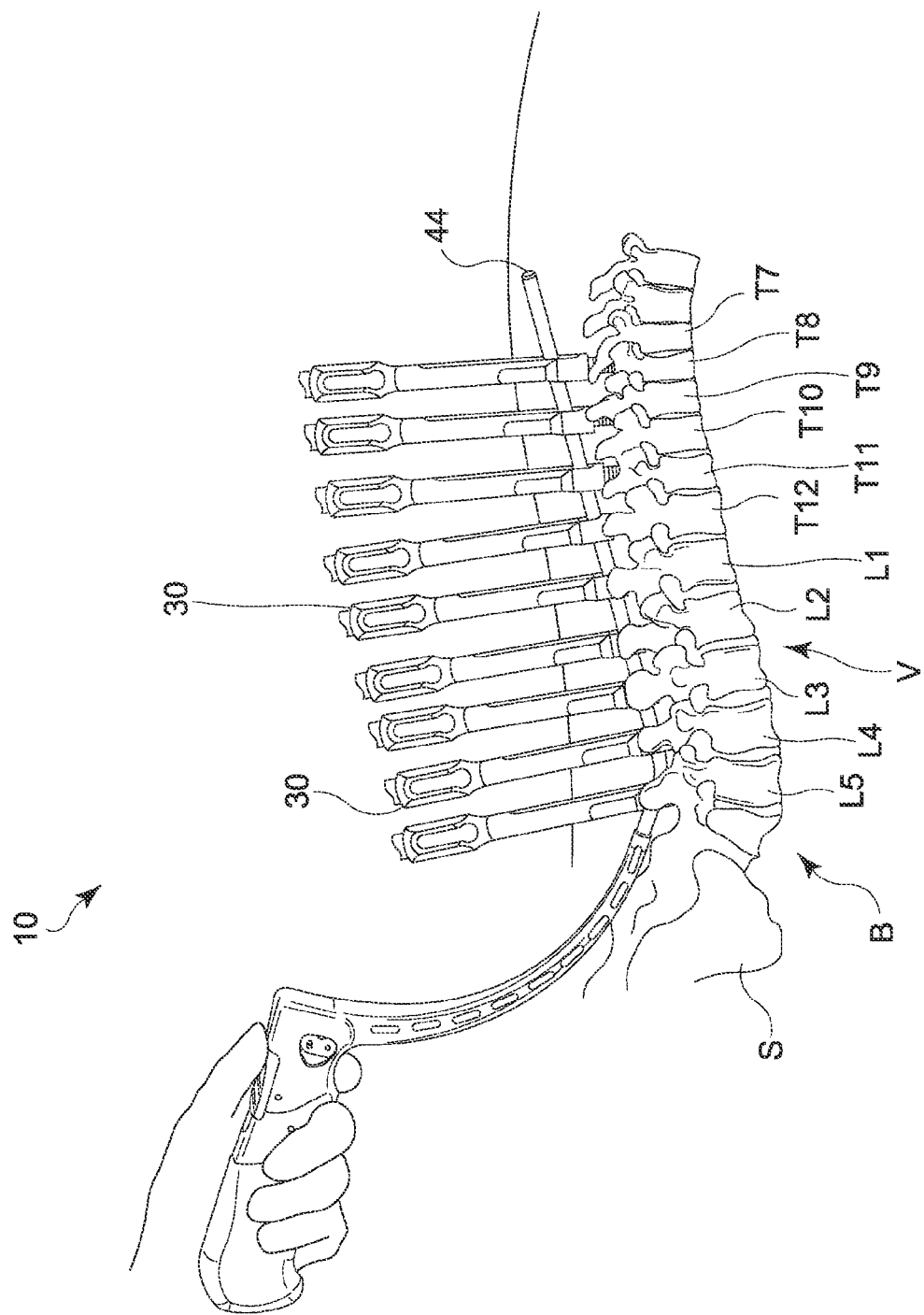
FIG. 10 is a plan view of components of one embodiment of a system in accordance with the principles of the present disclosure disposed with vertebrae.
Figure 11:
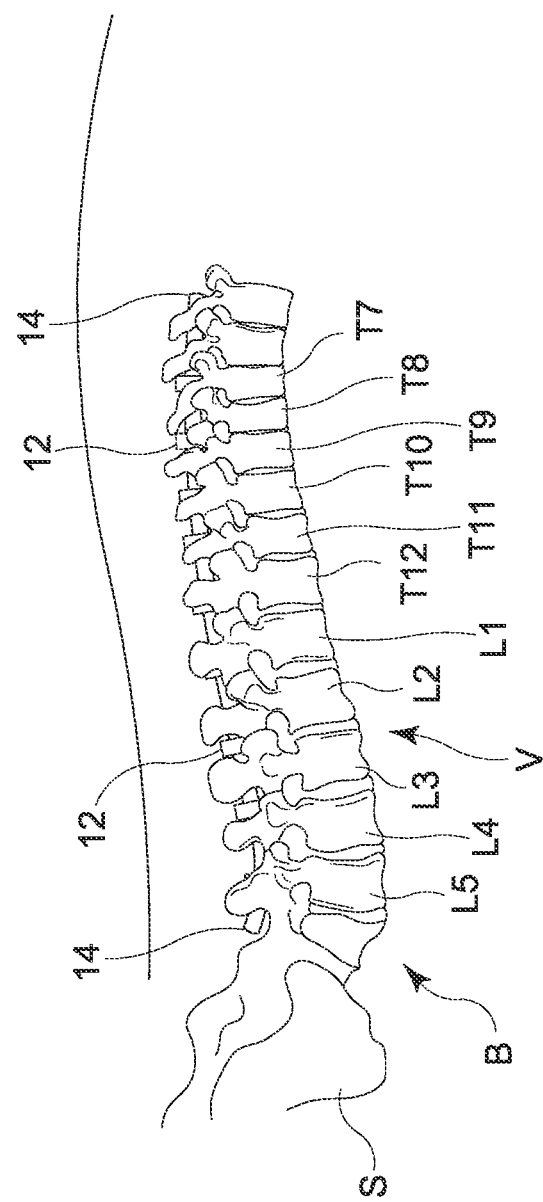
FIG. 11 is a plan view of components of one embodiment of a system in accordance with the principles of the present disclosure disposed with vertebrae.

In one embodiment, system 10 includes a rod gripper 70, as shown in FIG. 6, Rod gripper 70 includes a handle portion 72 configured to facilitate manipulation of gripper 70 and/or spinal rod 14. Rod gripper 70 includes a longitudinal portion 74 that extends between handle portion 72 and a gripping portion 76. In one embodiment, handle 72 is movable and configured to manipulate gripping end 76, such that when handle 72 is moved from a first configuration to a second configuration, gripping end 76 engages spinal rod 14.

In assembly, operation and use, as shown in FIGS. 5-11, spinal correction system 10, similar to the systems described herein, is employed with a surgical procedure, such as, for example, a correction treatment to treat spinal deformities, such as, for example, kyphosis of a spine. In some embodiments, one or all of the components of spinal correction system 10 can be delivered or utilized as a pre-assembled device or can be assembled in situ. Spinal correction system 10 may also be employed with other surgical procedures.

For example, spinal correction system 10 is employed with a surgical treatment for scoliosis correction of an affected section of a spinal column and adjacent areas within a body B of a patient, such as, for example, vertebrae V. In one embodiment, a portion of vertebrae V comprises thoracic vertebral levels T and a portion of vertebrae V comprises lumbar vertebral levels L. Body B includes a lateral portion LP and a contra-lateral portion CLP. In one example, thoracic vertebral levels T7-T12 comprise an apex of a scoliosis curvature and/or deformity. In some embodiments, spinal correction system 10 may be employed with one or a plurality of vertebrae.

In use, to treat vertebrae V, a medical practitioner obtains access to a surgical site including vertebrae V in any appropriate manner, such as through incision and retraction of tissues. In some embodiments, spinal correction system 10 can be used in any existing surgical method or technique including minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

Figure 5:
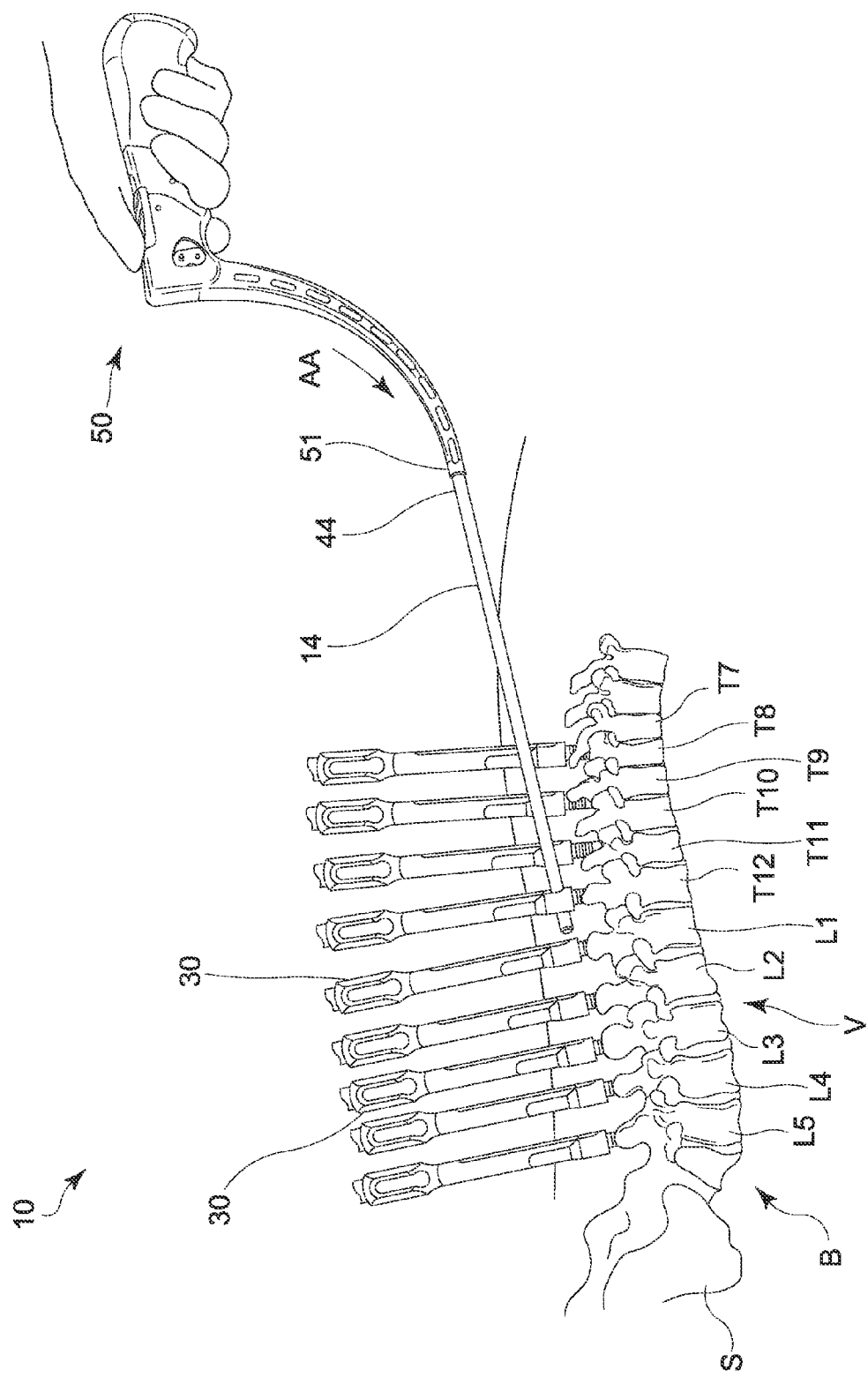
FIG. 5 is a plan view of components of one embodiment of a system in accordance with the principles of the present disclosure disposed with vertebrae.

One or a plurality of percutaneous incisions are made in body B and a cutting instrument (not shown) creates one or a plurality of surgical pathways and/or openings for implantation of components of spinal correction system 10. The percutaneous incisions are made in tissue of portions LP, CLP and disposed in a plane parallel to a sagittal plane SP, as shown in FIG. 5, of vertebrae V. The tissue of portions LP, CLP includes soft tissue comprising muscle, ligaments, tendons, cartilage and/or bone. Once access to the surgical site is obtained percutaneously, the components of spinal implant system 10 can be delivered or implanted with portions LP, CLP. A preparation instrument (not shown) can be employed to prepare tissue surfaces of vertebrae V, as well as for aspiration and irrigation of a surgical region.

Pilot holes (not shown) are made bilaterally in vertebrae V for receiving MAS 12. Shaft 18 of each MAS 12 is inserted, drilled or otherwise fixed to the vertebral levels of vertebrae V. Spinal correction system 10 includes implant supports, such as, for example, extenders and/or reduction instruments 30 that are applied to MAS 12 attached with vertebrae V on contiguous vertebrae, as shown in FIGS. 5-11. Instruments 30 are connected with MAS 12 attached with vertebrae V.

Instruments 30 are oriented for manipulation, alignment and capture of MAS 12. In some embodiments, one or a plurality of instruments 30 can be applied to a respective concave or convex portion of vertebrae V for performing one or a plurality of steps employing spinal correction system 10. In one embodiment, instruments 30 are disposed in series along vertebrae V such that an instrument is disposed with each vertebral level of a treated section. In one embodiment, instruments 30 are disposed on sequential and/or alternating vertebral levels of vertebrae V. In some embodiments, instruments 30 may be sequential and/or alternated over one or a plurality of vertebral levels of the thoracolumbar section of vertebrae V, such as, for example, across vertebrae T7-T12 and L1-L5.

An instrument release 32 of each instrument 30 is manipulated to move leg extensions 34 in an outward direction such that distal engagement parts 36 move outwardly and are disposed in an open position. Distal engagement parts 36 are brought into close proximity with receivers 16 of each of MAS 12 to provide engagement with each of MAS 12. Instrument release 32 is manipulated such that leg extensions 34 are moved inwardly and distal engagement parts 36 are disposed in a closed position to capture each of MAS 12 in releasable fixation. Leg extensions 34 define an opening, such as, for example, an elongated slot 38 that is disposed in alignment and communicates with passageway 22 to define a window 40.

Instruments 30 are applied to MAS 12 attached with levels T on portion LP, which includes a concave portion of vertebrae V. In some embodiments, instruments 30 are applied to MAS 12 attached with levels L on portion LP, which includes a convex portion of vertebrae V. In some embodiments, instruments 30 are applied to MAS 12 attached with levels T on portion CLP, which includes a convex portion of vertebrae V. In some embodiments, instruments 30 are applied to MAS 12 attached with levels L on portion CLP, which includes a concave portion of vertebrae V.

Spinal rod 14 is sequentially inserted along vertebrae V and attached to MAS 12 at a plurality of vertebral levels. Spinal rod 14 is inserted in a cephalad to caudal orientation, in the direction shown by arrow AA in FIGS. 5 and 6. In one embodiment, end 42 may be sharpened to facilitate insertion and movement through body B. In some embodiments, ends 42, 44 may include a locking element, such as, for example, a notch or groove, for attachment with an inserter 50 to maintain the orientation of spinal rod 14 relative to inserter 50 and/or vertebrae V during insertion of spinal rod 14.

End 44 of spinal rod 14 is attached with a distal end 51 of inserter 50 for insertion and positioning within body B, for example, as shown in FIG. 5, and passing spinal rod 14 along instruments 30 and/or MAS 12, Inserter 50 includes a handle 52 such that spinal rod 14 is manipulated for insertion into body B, as shown in FIG. 3. Inserter 50 is configured to percutaneously move spinal rod 14 along vertebrae V. In one embodiment, end 42 is inserted into body B in a cephalad to caudal orientation, in the direction shown by arrow AA in FIGS. 5 and 6, and through a window 40 of a first instrument 30/MAS 12 attached to a vertebral level, such as for example, T7. Spinal rod 14 is translated through window 40 of instrument 30/MAS 12 and relative to MAS 12. In one embodiment, spinal rod 14 is passed along vertebral levels L1-L5 and T7-T12 between vertebrae V and the fascia.

Spinal rod 14 is moved caudally through window 40 of the first instrument 30/MAS 12 such that end 42 is sequentially inserted into and through a window 40 of a second instrument 30/MAS 12 attached to a vertebral level positioned caudally to T7, such as, for example, T8 or T9. Spinal rod 14 is similarly moved through windows 40 of third and fourth instruments 30/MAS 12 such that end 42 is sequentially inserted into and through the windows 40 of the third and fourth instruments 30/MAS 12 attached to vertebral levels T10, T11. In one embodiment, spinal rod 14 is moved through windows 40 of instruments 30/MAS 12 such that end 42 is inserted through the windows 40 of instruments 30/MAS 12 attached to sequential vertebral levels, T12, L1, L2, L3, L4, and/or L5. In some embodiments, insertion of spinal rod 14 is performed percutaneously by manipulating handle 52 in a free hand delivery technique. In some embodiments, movement of spinal rod 14 through windows 40 and/or body B can be monitored using navigation, fluoroscopy imaging techniques and/or tactile feedback.

With inserter 50 attached and spinal rod 14, as described herein, handle 52 is manipulated and spinal rod 14 is moved and/or translated to a selected position relative to vertebrae V, which includes a selected sagittal and/or coronal rod position relative to vertebrae V, for correction of vertebrae V. Instruments 30 each include reducers 60, as shown in FIGS. 2 and 3, configured to dispose spinal rod 14 with receivers 16 of MAS 12. Each reducer 60 includes a handle 62 manipulable to align reducer 60 with an interior passageway of each of instruments 30. Reducer 60 has an outer surface 64 that is threaded with an inner surface of each of instruments 30. Reducer 60 is rotated to translate reducer 60 axially, in a proximal or distal direction relative to instrument 30. Reducer 60 is translated such that an end surface 66 engages spinal rod 14 in a configuration to move spinal rod 14 distally to drive spinal rod 14 into passageways 22 of receivers 16.

In one embodiment, spinal rod 14 is advanced caudally until end 42 extends past the most caudal sequential instrument 30 attached to vertebral level L5, as shown in FIG. 6. Spinal rod 14 is provisionally seated within receivers 16 such that inner surfaces 20 are movable relative to outer surface 24 and receivers 16 are movable relative to shafts 18. Inserter 50 is attached to spinal rod 14 to maintain spinal rod 14 in the selected orientation, rod gripper 70 is passed through a percutaneous opening adjacent L5 and manipulated to grip spinal rod 14 adjacent end 42 and facilitate movement of spinal rod 14 such that when handle 72 is moved from a first configuration to a second configuration, gripping end 76 engages spinal rod 14.

Spinal rod 14 is moved caudally such that a selected length of spinal rod 14 extends beyond the most caudal instrument 30/MAS 12 attached to a vertebral level L5. Portion 41 of spinal rod 14 is bent to a selected curvature. A rod bender, not shown, is passed through a percutaneous opening adjacent L5 and utilized to bend portion 41 of spinal rod 14 to a selected curvature. The rod bender is configured to engage spinal rod 14 and apply a selected force to form a selected curvature to portion 41. In one embodiment, the selected curvature of portion 41 substantially conforms to a curvature of vertebral levels L1-L5.

Upon deformation and bending of the selected curvature to portion 41, inserter 50 and rod gripper 70 are removed from end 44 of spinal rod 14 and inserter 50 is passed through a percutaneous opening adjacent L5 and attached to end 42. Inserter 50 is manipulated such that end 44 is below the fascia and above vertebrae V.

A force is applied to inserter 50 to advance spinal rod 14 cephalically toward vertebral level T7. Spinal rod 14 is moved cephalically through window 40 of a first instrument 30/MAS 12 attached to a vertebral level, such as, for example, vertebral level T12, such that end 44 is sequentially inserted into and through a window 40 of a second instrument 30/MAS 12 attached to a vertebral level positioned cephalically to T12, such as, for example, T11 or T10. Spinal rod 14 is similarly moved through windows 40 of third and fourth instruments 30/MAS 12 such that end 44 is sequentially inserted into and through the windows 40 of the third and fourth instruments 30/MAS 12 attached to cephalic vertebral levels, such as, for example, vertebral levels T9 and/or T8. In one embodiment, spinal rod 14 is moved through windows 40 of instruments 30/MAS 12 such that end 44 is inserted through the windows 40 of instruments 30/MAS 12 attached to sequential vertebral level T7.

In some embodiments, portion 43 of rod 14 disposed with one or more of levels T7-T12 may be selectively bent for a correction treatment of vertebrae V, similar to that described herein, by passing a rod bender through a percutaneous opening adjacent T7 and bending portion 43. A rod bender, not shown, is passed through a percutaneous opening adjacent T7 and utilized to bend portion 43 of spinal rod 14 to a selected curvature. The rod bender is configured to engage spinal rod 14 and apply a selected force to form a selected curvature to portion 43. In one embodiment, the selected curvature of portion 41 substantially conforms to a curvature of vertebral levels T7-T12.

In some embodiments, reducers 60 may reduce spinal rod 14 with various MAS 12 incrementally, continuously to engagement with spinal rod 14 and/or to disengagement from spinal rod 14, during the various steps of the correction treatment. With inserter 50 attached and spinal rod 14 disposed in windows 40, as described herein, reducers 60 are manipulated to draw receivers 16 of MAS 12, which includes vertebral levels T7-T12 and L1-L5, up to receive spinal rod 14, in the direction shown by arrow EE in FIG. 2. Spinal rod 14 is selectively and provisionally reduced within passageways 22 such that spinal rod 14 is disposed in the selected orientation relative to vertebrae V, for example, in a sagittal plane of vertebrae V offset from plane SP for correction of vertebrae V. In one embodiment, spinal rod 14 is secured to each MAS 12 through the use of a coupling member, such as, for example a set screw, threaded with receiver 16.

In some embodiments, a guide wire and/or a trocar-cannula assembly may be employed as an instrument for gaining access to the surgical site and/or defining the pedicle trajectory. The guide wire is introduced along the pedicle trajectory before delivering the fasteners. The fasteners are translated over the guide wire to be delivered to vertebrae V. In one embodiment, an interbody implant (not shown) is delivered along a direct lateral surgical approach or pathway adjacent to a surgical site and implanted adjacent selected vertebral levels.

Upon completion of a procedure, described herein, the surgical instruments, assemblies and non-implanted components of spinal correction system 10 are removed and the incisions are closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed with adult deformity surgery, and/or treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the dams appended hereto.

What is claimed is:

1. A method for treating a spine, the method comprising the steps of:
    fastening at least one fastener with a first vertebra, a second fastener to a second vertebra, and a third fastener to a third vertebra, wherein the second vertebra is between the first and third vertebra;
    providing a longitudinal element having a first portion and a second portion;
    passing the first portion of the longitudinal element through the second and third fasteners such that the second portion of the longitudinal element extends from the second fastener through the third fastener;
    bending the first portion of the longitudinal element to a selected curvature; and
    moving the second portion of the longitudinal element through the second fastener to the first fastener after the first portion of the longitudinal element has been passed through the second and third fasteners.

2. A method for treating a spine as recited in claim 1, wherein the step of fastening includes fastening the first fastener with a thoracic vertebra.

3. A method for treating a spine as recited in claim 1, wherein the step of fastening includes fastening the first fastener with a lumbar vertebra.

4. A method for treating a spine as recited in claim 1, further comprising the step of providing at least one implant support connected with the second fastener.

5. A method for treating a spine as recited in claim 4, wherein the step of moving along portions of the vertebrae includes translating the longitudinal element within the at least one implant support and relative to the at least one fastener.

6. A method for treating a spine as recited in claim 1, further comprising at least one implant support connected with the first fastener and the second fastener.

7. A method for treating a spine as recited in claim 6, wherein the step of passing includes translating the longitudinal element within at least one implant support and relative to the first fastener and second fastener.

8. A method for treating a spine as recited in claim 1, wherein the first vertebra includes thoracic vertebra and the third vertebra includes lumbar vertebrae.

9. A method for treating a spine as recited in claim 8, wherein the step of moving includes introducing the longitudinal element adjacent T12 and moving the longitudinal element along L-L5 to extend from at least one fastener adjacent L5.

10. A method for treating a spine as recited in claim 8, wherein the longitudinal element is passed along L1-L5 and T7-T12 between the vertebrae and fascia.

11. A method for treating a spine as recited in claim 8, wherein the selected curvature substantially conforms to a curvature of L1-L5.

12. A method for treating a spine as recited in claim 1, further comprising the step of providing an inserter connectable to the longitudinal element for moving the longitudinal element.

13. A method for treating a spine as recited in claim 12, wherein the inserter is configured to percutaneously move the longitudinal element.

14. A method for treating a spine as recited in claim 12, further comprising the step of providing a rod gripper engageable with the first portion for moving the longitudinal element.

15. A method for treating a spine as recited in claim 14, wherein the rod gripper moves the longitudinal element in a caudad direction.

16. A method for treating a spine as recited in claim 1, wherein the step of moving the longitudinal element is in a caudad direction and the step of moving along the portions includes moving the longitudinal element in a cephalad direction.

17. A method for treating a spine as recited in claim 1, further comprising the step of reducing the second portion of the longitudinal element with the second fastener such that the vertebra is derotated.

* * * * *

UNITED STATES PATENT AND TRADEMARK OFFICE
CERTIFICATE OF CORRECTION

PATENT NO. : 9,924,983 B2  
APPLICATION NO. : 14/619965  
DATED : March 27, 2018  
INVENTOR(S) : Anand Page 1 of 1

It is certified that error appears in the above-identified patent and that said Letters Patent is hereby corrected as shown below:

In the Specification

In Column 1, Line 4, delete "TECHNICAL HELD" and insert -- TECHNICAL FIELD --, therefor.

In Column 3, Line 1, delete "111" and insert -- T11 --, therefor.

In Column 4, Line 17, delete "dearly" and insert -- clearly --, therefor.

In Column 5, Line 27, delete "elastorneric composites," and insert -- elastomeric composites, --, therefor.

In Column 5, Line 39, delete "(TOP)," and insert -- (TCP), --, therefor.

In Column 8, Line 8, delete "FIG. 6," and insert -- FIG. 6. --, therefor.

In Column 9, Line 56, delete "MAS 12," and insert -- MAS 12. --, therefor.

In Column 12, Line 33, delete "dams" and insert -- claims --, therefor.

In the Claims

In Column 12, Line 38, in Claim 1, delete "fastening at least one fastener with a first vertebra," and insert -- fastening a first fastener to a first vertebra, --, therefor.

In Column 13, Line 15, in Claim 9, delete "L-L5" and insert -- L1-L5 --, therefor.

Signed and Sealed this  
Twenty-first Day of August, 2018

Andrei Iancu  
*Director of the United States Patent and Trademark Office*